United States Patent [19]

Vetter

[11] Patent Number: 4,874,381
[45] Date of Patent: Oct. 17, 1989

[54] HYPODERMIC SYRINGE

[75] Inventor: Udo J. Vetter, Ravensburg, Fed. Rep. of Germany

[73] Assignee: Arzheimittel GmbH Apotheker Vetter & Co. Ravensburg, Ravensburg, Fed. Rep. of Germany

[21] Appl. No.: 211,229

[22] Filed: Jun. 24, 1988

[30] Foreign Application Priority Data

Feb. 16, 1988 [EP] European Pat. Off. ...... 88 102.236.2

[51] Int. Cl.⁴ ............................................. A61M 5/08
[52] U.S. Cl. ...................... 604/191; 604/91; 604/208
[58] Field of Search ............... 604/191, 211, 218, 224, 604/82, 89, 90, 91, 207, 208, 210; 600/4, 5; 222/136

[56] References Cited

U.S. PATENT DOCUMENTS

| 2,549,417 | 4/1951 | Brown | 604/90 |
| 2,591,046 | 4/1952 | Brown | 604/90 |
| 4,226,236 | 10/1980 | Genese | 604/89 |
| 4,312,343 | 1/1982 | LeVeen et al. | 604/211 |
| 4,583,974 | 4/1986 | Kokernak | 604/211 |
| 4,613,326 | 9/1986 | Szwarc | 604/89 |
| 4,792,329 | 12/1988 | Schreuder | 604/90 |

FOREIGN PATENT DOCUMENTS 1214053 12/1970 United Kingdom ................. 604/82

Primary Examiner—C. Fred Rosenbaum
Assistant Examiner—Mark O. Polutta
Attorney, Agent, or Firm—Herbert Dubno

[57] ABSTRACT

A two-compartment syringe having a bypass through which the liquid can be forced into the medicament compartment by advance of the piston connected to the stem, has a brake retarding the displacement of this piston until it reaches the bypass to prevent undesired discharge of the injectable substance from the syringe. Once the latter piston has reached the bypass, the stem can be axially displaced independently of a braking action by the damping means for normal injection.

10 Claims, 1 Drawing Sheet

HYPODERMIC SYRINGE

FIELD OF THE INVENTION

My present invention relates to a syringe for medicinal purposes and, more particularly, to a double-piston syringe of the type in which a compartment containing a liquid can be connected to a compartment containing an agent to be dissolved or entrained in the liquid so that the resulting combination can be ejected from the needle of the syringe. More particularly, the invention relates to a syringe of the type in which a cylinder or barrel is provided at one end with a formation or fixture for attaching the ejection needle and from the other end of which, the stem of a plunger can emerge for displacement utilizing a customary syringe operation in which the barrel is grasped by the user as a finger displaces the plunger to effect injection.

BACKGROUND OF THE INVENTION

A syringe of the two-compartment type embodying the structure described above and wherein a bypass is provided through which the liquid can be forced to flow into the compartment containing an agent to be dispersed in that liquid, is described in Europatent publication No. 85 101 508.

In this syringe, one plunger part forms a partition between the two compartments while the other plunger part is attached to the stem and, as the stem is advanced, the second plunger part displaces the liquid and the first plunger part past the bypass until the two plunger parts abut one another, whereupon the plunger formed by these parts is displaced by the stem to eject the composition from the needle.

The syringe described in the Europatent publication is a so-called disposable syringe which is sterilized and prefilled with the injectable substance in the two-component state.

Such two-compartment syringes have been found to be especially effective when the injectable substance is to be in the form of a mixture in a liquid phase or a solution of a component in the liquid which has only a limited effective life in the liquid composition and thus must be fabricated as shortly before use as is possible.

The two components are thus provided in separate compartments and remain stable in these compartments for long periods of time.

Since one compartment is provided axially behind the other and the two substances are only brought into contact with each other immediately prior to injection, it is necessary to provide a means for permitting the liquid from the compartment most distal from the needle to mix with the solid substance, for example, in the compartment proximal to the needle.

This is achieved by providing the bypass immediately ahead of the plunger member which delimits the liquid compartment at its side closest to the needle.

Consequently, as the plunger stem is activated, i.e. displaced into the cylinder or barrel of the syringe, the plunger part most distal from the needle will drive the body of liquid ahead of it and the other plunger part toward the needle until communication is established between the compartments between the plunger parts and the compartment containing the solid component ahead of the plunger parts and between the latter and the needle.

The bypass thus serves to allow transfer of the liquid substance from the upstream compartment to the downstream compartment for mixing with the solid substance when the plunger part separating the two compartments is shifted toward the needle-end of the barrel to an extent sufficient to allow the bypass to communicate between the compartments around this plunger part.

The drawback of this type of syringe, however, is that with an excessive pressure upon the stem or rod of the piston, the liquid can be transferred through the bypass with an excessive velocity so that the substance within the compartment at the downstream side of the bypass will be forced from the needle passage out of the syringe in an uncontrolled manner. This can lead to undesired contamination of the user of the syringe as well as of the patient and may be detrimental to the patient if the administration of a precise quantity of a medicament is essential.

OBJECTS OF THE INVENTION

It is, therefore, the principal object of the present invention to provide a syringe of the two-compartment type described whereby the aforementioned disadvantages are obviated.

Another object of this invention is to provide a syringe in which the flow velocity of the liquid phase into the solid phase compartment can be controlled independently of the rate at which the mixture or solution formed in the solid-phase compartment is administered to the patient.

SUMMARY OF THE INVENTION

These objects and others which will become apparent hereinafter are attained, in accordance with the invention, in a syringe of the type generally described above and in which a plunger brake is provided at the end of the syringe body remote from the needle to form a velocity-damping means which limits the rate at which the plunger can be displaced until the plunger member affixed to the stem reaches the bypass.

Stated otherwise, the braking device permits only a limited stroke velocity of the stem and the plunger members until the plunger member affixed to the stem reaches the bypass.

The syringe can comprise a cylindrical syringe body formed at one end with a fitting adapted to receive a needle and open at an opposite end to permit the stem to extend from the syringe body.

The stem carries a plunger body most distal to the needle and which is axially affixed to the stem or piston rod.

Ahead of the plunger body affixed to the stem, is a mass of the liquid component in the liquid compartment which is also delimited by the second plunger member spaced in the downstream direction ahead of the first-mentioned plunger member. The second plunger member, of course, bounds also the downstream compartment which contains the solid substance and communicates with the needle.

Advantageously, the brake is provided between the stem and the syringe body, e.g. via a cap or insert which is fitted onto the end of the syringe body most distal from the needle.

The advantage of the system of the invention is that the limitation of the speed of displacement of the piston or plunger during the initial period of displacement until the upstream plunger body reaches the bypass, ensures a comparatively slow feed of liquid in a controlled manner into the downstream compartment for mixture with and, if appropriate, dissolution of the solid substance. Once the upstream plunger body reaches the bypass and substantially all of the liquid has been expressed from the upstream compartment, the brake can disengage and can no longer interfere with the manual displacement of the stem by axial pressure and hence the plungers in the direction of the needle. The uncontrolled discharge of the injectable substance from the needle or the needle fitting is thus prevented during the initial stage while there is full control over the injection operation after the injectable substance has been fully formed.

The controlled or delayed combination of the liquid phase with the solid phase ensures that there will be sufficient time for the solid phase to enter into solution in the liquid phase so that a more homogeneous combination as the injectable substance can be formed.

The damping element can be a closure cap for the end of the syringe body remote from the needle and can have radially extending edge portions which can provide a finger rest beneath which the fingers of the user can engage when the stem is to be displaced by the thumb of the user.

The brake itself can be formed by an internal thread on this cap which threadedly engages an external or male thread on the stem, extending only a fraction of the length thereof toward the free end of this stem.

The length of the threaded portion of the shank or stem is so located that the inner thread of the cap will disengage from the threaded shank just as the upstream plunger body at its upstream edge reaches the bypass.

In order to displace the liquid, therefore, from the upstream compartment to the downstream compartment, the stem must be rotated to axially drive the plungers toward the needle end of the syringe by the threaded engagement of the shank and the internal thread. Since high-speed rotation of the stem is not possible, it will be apparent that a comparatively slow displacement of the upstream plunger body is effected and a comparatively low velocity of the liquid through the bypass is generated. As soon as the thread of the shank is released by the internal thread of the cap, a simple axial displacement of the stem and of the plungers is possible for the normal injection.

Advantageously, the diameter of the piston stem, in the region upstream of the threaded portion should be only slightly smaller than the lumen or clear diameter of the internal thread. This means that the crests of the internal thread of the cap will serve to guide the stem and the piston or plunger.

Advantageously, the distal plunger body, i.e. the plunger body which is axially affixed to the stem, can have a blind bore in which an internal thread can be formed, e.g. by an internally threaded end of the stem so that the mating threads, which can be cut in the plunger body by the male thread of the stem, can anchor the upstream plunger body on the stem.

Preferably the thread anchoring the plunger body to the stem is of the same hand or sense as the thread which drives the plunger by rotation of the stem during the initial part of the travel of the plunger bodies is described. This means that the stem can be simply screwed into the piston. When the thread in the piston is undercut so that the threaded end of the stem passes beyond the internal thread in the piston, after assembly, free rotation of the stem within the piston is permitted without rotation of the latter to effect the screw action which drives the piston toward the needle end.

Finally, according to the invention, the cap can be formed with a collar which extends axially into the syringe body or cylinder and on the inner side of which the internal thread cooperating with the threaded shank of the stem engages. The collar can form with the wall of the cylinder body an annular groove in which residues of the injectable substance from the bypass can collect and thereby prevent contamination of the user by the escaping injection solution.

BRIEF DESCRIPTION OF THE DRAWINGS

The above and other objects, features and advantages of the present invention will become more readily apparent from the following description, reference being made to the accompanying drawing in which.

SPECIFIC DESCRIPTION

Figure 1:
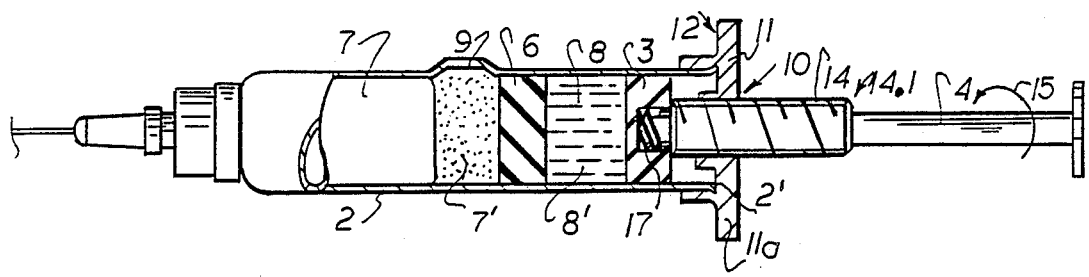
FIG. 1 is an axial cross sectional view, partly in elevation of the syringe during the initial stages of activation of the plunger.

The syringe shown in the drawing for medicinal purposes comprises a fitting 5 formed at one end of the syringe barrel or cylinder 2 which may have a Luer-like projection, adapted to receive an injection needle 1. At the right-hand end of the syringe body 2, i.e. the end remote from the needle, the stem 4 of a piston projects from the syringe body.

The syringe piston 3 is axially fixed to the stem 4 and is slidable in the syringe body 2 and is located upstream of a second piston 6 so that that liquid compartment 8 is defined between the two pistons 3 and 6 which also can be referred to as plungers or plunger bodies for the purposes of this application.

The plunger body 6 is likewise axially shiftable and forms the right-hand boundary of a compartment 7, also referred to as a downstream compartment. In the wall of the cylinder or body 2, a bypass 9 is formed.

As a result, the syringe has a two-compartment syringe of a type which must be used when the mixture of the liquid phase 8 with a solid phase 7' within the compartment 7 is unstable over long periods or, stated otherwise, has limited stability. The mixture or solution has been shown at 7" in FIGS. 2 and 3.

Naturally, it is presumed that the solid substance 7' and the liquid phase 8', which can be a solvent for the solid phase, are stable when held separate by the plunger member 6 in which the initial state (FIG. I) forms a partition between the two substances.

The syringe is usually a single-use or disposable syringe which can be filled with the substances 7', 8' in a sterile state or can be sterilized after the substances have been introduced.

The syringe in the form shown in FIG. 1 can be packaged, stored and distributed for use.

The two compartments 7 and 8 are disposed axially one behind the other and must be interconnected through the bypass 9 to form the injectable substance 7", e.g. the solution. In other words, the liquid 8' in compartment 8 must be caused to flow through the bypass 9 into the downstream compartment 7 proximal to the needle to that the desired mixture or solution can form.

The bypass 9 has an axial length, therefore, which exceeds the axial length of the plunger member 6 and can otherwise be formed as a radially outward bulge in the wall of the injection cylinder or syringe body 2.

Figure 2:
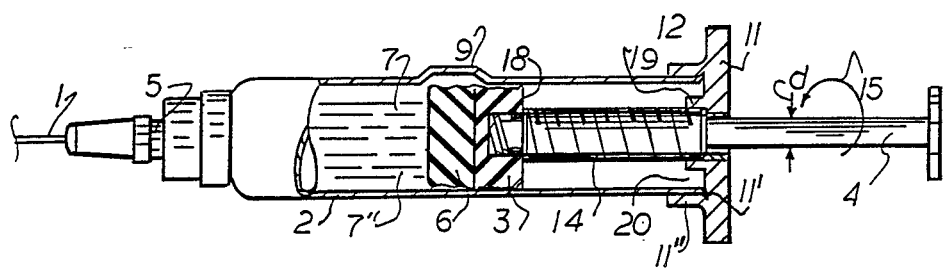
FIG. 2 is a similar view of the syringe after the contents of the liquid compartment have been displaced into the downstream compartment.

To bring the two compartments 7 and 8 into communication via the bypass 9, the second piston 6 must be shifted toward the needle and 5 to the extent that the two ends of the bypass 9 will open to opposite sides of the piston 6 as can be seen from FIG. 2.

On the syringe body 2, at its end opposite the needle-fitting end 5, according to the invention, I provide a piston brake which has been represented generically at 10 and which serves to damp the speed with which the piston 3 can be displaced to the left It is important that this limitation of the speed be maintained until the piston 3 has reached the bypass 10 (FIG. 2).

Advantageously, the brake or damper 10 is formed by a closure cap 11 which can be forced over the right-hand end of the syringe body 2, i.e. the end distal to the needle-fitting end 5.

The syringe body may have an outwardly turned lip 2' which engages in a groove 11' of the cap 11 at the junction of the apron 11' of this cap which fits over the syringe body 2.

The cap 11 also is formed with a radially outwardly extending flange 11a which forms finger holds 12 so that the index finger and the middle finger of the user can grip beneath the finger holds 12 as the plunger stem 4 is displaced inwardly by the thumb for injection in the usual manner.

In addition, the closure cap 11 is provided with an internal thread 13 which is threadedly coupled with the external thread 14 extending over a limited portion of the length of the stem 4 and a region referred to as the threaded shank thereof.

The length of the threaded shank 14 is so dimensioned that the end 14.1 of the threaded shank turned away from the piston 3 passes out of the internal thread 13 when the piston 3 has reached the bypass 9, i.e. the upstream end of the piston 3 is located substantially at the upstream end of the bypass 9.

Consequently, simple axial displacement of the stem is prevented as long as the threaded portions 13 and 14 remain engaged and, in order to move the piston 3 from the position shown in FIG. 1 to the position shown in FIG. 2, it is necessary to rotate the stem 3 about its longitudinal axis as has been represented by the arrow 15. Such rotation causes advance of the piston to the left and a controlled slow flow of liquid from the upstream compartment 8 into the downstream compartment 7.

Figure 3:
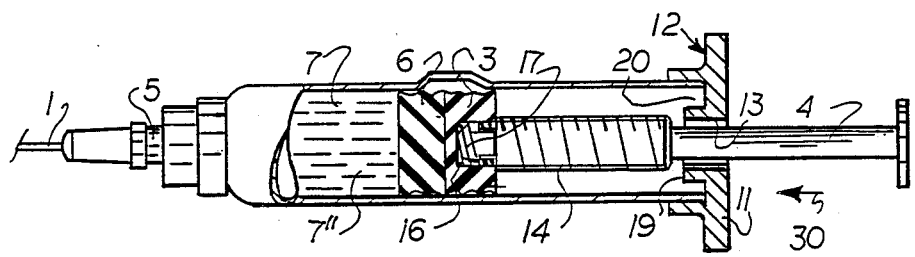
FIG. 3 is an axial section of the syringe in its position preparatory to injection of the mixed solution into the patient.

As a consequence, no rapid discharge of the injectable substance in an uncontrolled way from the needle to the exterior can occur. As soon as the threaded shank 14 disengages from the internal thread 13 (FIG. 3), the liquid displacement is complete. The injectable substance 7" by simple axial displacement of the stem 4 as represented by arrow 30 (FIG. 3).

The diameter d of the stem 4 axially upstream of the threaded shank should be only slightly smaller than the clear or lumen diameter of the internal thread 13 so that the crests of the internal thread essentially can form a guide for the stem during the axial displacement thereof thereby facilitating the injection operation.

The piston 3 is provided with an axially opening blind bore 16 for a threaded stud 17 on the end of the stem 4. The blind bore is provided adjacent its mouth with an internal thread 18 which can engage threadedly the stud 17, but beyond this thread 18 is cut away so that once the thread portion of stud 17 passes the screw thread 18, the stem 4 can freely rotate with rotatable entrainment of the piston 3. This free rotation facilitates the threaded displacement of the portion 14 in the internal thread 13 of the cap.

The cap 11, moreover, is provided with a collar 19 which extends axially into the syringe body 2 and continues the internal thread 13 inwardly. This collar 19 defines an annular groove 20 in which any residue discharged from the bypass can collect so that it cannot emerge from the syringe body at its end remote from the needle and contaminate the user.

I claim:

1. A medicinal syringe, comprising:
    a generally cylindrical syringe body formed with a first end having a needle-receiving fitting, a second and opposite said first end and a bypass intermediate said ends;
    a first piston slidable in said body proximal to said second end;
    a second piston slidable in said body between said first piston and said first end, said pistons defining a liquid compartment between them adapted to communicate with a downstream compartment between said second piston and said first end through said bypass upon displacement of said second piston so that opposite sides thereof are bridges by said bypass;
    a piston-actuating stem axially engaged by said first piston, extending out of said second end and axially displaceable to drive said pistons toward said first end of said body; and
    velocity damping means formed at said second end or said body for restricting a velocity of displacement of said first piston substantially until said first piston reaches said bypass, thereby limiting a velocity with which liquid from said liquid compartment enters said downstream compartment, and thereafter disengaging to permit less-braked axial displacement of said pistons by said stem, said damping means including a cap fitted onto said second end and formed with a central bore having an internal screwthread, said stem having over part of its length an axially extend in shank having an external screwthread threadedly engaging said internal screwthread, and shank having a length such that said external screwthread passes out of said internal screwthread upon rotation of said stem to advance said first piston as said first piston reaches said bypass.

2. The syringe defined in claim 1 wherein said cap is formed with a radially extending flange forming fingerholds for gripping of the syringe by a user.

3. The syringe defined in claim 2 wherein said stem has an outer diameter upstream of said shank which is only slightly smaller than the clear inner diameter of said internal screwthread.

4. The syringe defined in claim 3 wherein said first piston is formed with a blind axial bore rotatably receiving an inner end of said stem.

5. The syringe defined in claim 4 wherein said blind axial bore is formed with an internal screwthread adjacent a mouth of said blind axial bore and is undercut beneath said internal screwthread adjacent said mouth, said inner end of said stem, being formed with an externally threaded stud engageable with said internal screwthread adjacent said mouth and passing beneath said internal screwthread adjacent said mouth to enable rotation of said stem without rotatable entrainment of said first piston while axially locking said first piston on said stem.

6. The syringe defined in claim 5 wherein said cap is formed with a collar extending axially into said body and provided with said central bore, said collar defining with a wall of said body an annular groove for collecting an injectable substance discharged from said bypass behind said first piston.

7. The syringe defined in claim 4 wherein said cap is formed with a collar extending axially into said body and provided with said central bore, said collar defining with a wall of said body an annular groove for collecting an injectable substance discharged from said bypass behind said first piston.

8. The syringe defined in claim 3 wherein said cap is formed with a collar extending axially into said body and provided with said central bore, said collar defining with a wall of said body an annular groove for collecting an injectable substance discharged from said bypass behind said first piston.

9. The syringe defined in claim 2 wherein said cap is formed with a collar extending axially into said body and provided with said central bore, said collar defining with a wall of said body an annular groove for collecting an injectable substance discharged from said bypass behind said first piston.

10. The syringe defined in claim 1 wherein said cap is formed with a collar extending axially into said body and provided with said central bore, said collar defining with a wall of said body an annular groove for collecting an injectable substance discharged from said bypass behind said first piston.

* * * * *